United States Patent
Boncan et al.

(10) Patent No.: US 7,743,674 B2
(45) Date of Patent: Jun. 29, 2010

(54) HIGH TEMPERATURE FLUID TEST INSTRUMENT

(75) Inventors: Virgilio Go Boncan, Spring, TX (US); Dan Thomas Mueller, Cypress, TX (US)

(73) Assignee: BJ Services Company, Houston, TX (US)

( * ) Notice: Subject to any disclaimer, the term of this patent is extended or adjusted under 35 U.S.C. 154(b) by 459 days.

(21) Appl. No.: 11/651,089

(22) Filed: Jan. 8, 2007

(65) Prior Publication Data

US 2008/0163703 A1 Jul. 10, 2008

(51) Int. Cl.
*G01N 17/00* (2006.01)

(52) U.S. Cl. ..................................... 73/865.6

(58) Field of Classification Search .................. None
See application file for complete search history.

(56) References Cited

U.S. PATENT DOCUMENTS 7,128,142 B2  10/2006  Heathman et al.
7,128,149 B2  10/2006  Heathman et al.
2006/0060381 A1 *  3/2006  Heathman et al. ............... 175/7

OTHER PUBLICATIONS

Chandler Engineering, Water-Wetting Capability Tester, 2-page brochure entitled "Drilling Fluids-Viscosity", copyright 2005.

* cited by examiner

*Primary Examiner*—Robert R Raevis
(74) *Attorney, Agent, or Firm*—Howrey LLP

(57) ABSTRACT

An apparatus that can determine the water wettability of fluid at simulate downhole conditions. For example, a spacer fluid and a drilling mud mixture can be tested under a specified pressure and a specified temperature that simulate downhole conditions. Additionally, a shear rate may be applied to the fluid mixture that is substantially identical to the shear rate that will be exerted on the mixture due to downhole geometries and conditions. The apparatus may also provide the viscosity of the fluid under the designated pressure, at the specific temperature, and under the specified shear rate. The apparatus may also be used to determine the amount of spacer fluid that would need to be added to a drilling mud to improve the rheological properties of the mixture to provide adequate water wettability as well as the displacement of the mixture during the cementing process of a wellbore.

40 Claims, 1 Drawing Sheet

HIGH TEMPERATURE FLUID TEST INSTRUMENT

BACKGROUND OF THE INVENTION

1. Field of the Invention

The present invention relates generally to an apparatus that can determine the viscosity and water wettability of a spacer fluid and drilling mud mixture at downhole shear rate conditions. For example, the spacer fluid and drilling mud mixture can be tested under a specified pressure, at a specified temperature, and a shear rate may be applied to the mixture that is substantially identical to the shear rate that will be exerted on the mixture due to downhole geometries and conditions. The apparatus may also provide the viscosity of the spacer fluid and drilling mud mixture under a designated pressure, at a specific temperature, and under a specified shear rate. The apparatus may be used to determine the optimal composition and amount of spacer fluid that needs to be added to drilling mud to improve the rheological properties of the mixture to provide adequate water wettability as well as displacement of the drilling mud during the cementing process of a wellbore.

2. Description of the Related Art

Oil and gas wells typically include steel casing or steel tubing, hereinafter steel casing, cemented into the wellbore to provide support to the wellbore and prevent the wellbore from collapsing. The steel casing also allows for a hydraulic seal to be maintained within the wellbore to hydraulically isolate different sections of the well. The cement is important to support the wellbore formation as well as to help protect the steel casing from being damaged.

The first process in creating an oil or gas well is to drill the wellbore or at least a portion of the wellbore. The industry typically uses a drilling mud to aid in the drilling process to remove the drill cuttings from the wellbore. Drilling mud is generally water based mud or oil based. An oil based drilling mud does not provide sufficient water wettability properties, which may result in improper displacement of the drilling mud during the cementing process as well as possibly a decrease in the shear bond strength of the cement.

After the wellbore has been drilled to the desired depth, the drilling apparatus is removed and steel casing is inserted into the wellbore. The insertion of the steel casing displaces the drilling mud both between the steel casing and the wellbore as well as inside the steel casing. Cement is then pumped into the wellbore to cement in the steel casing. The cement within the wellbore needs to have adequate strength to support axial casing loads that may be present throughout the life of the well. It is known that the shear bond strength of the cement decreases if the wellbore is oil wet during the cementing process in comparison to a wellbore that is water wet. Thus, an oil based drilling mud may lower the shear bond strength of the cement if proper steps are not taken to ensure the wellbore is water wet. A spacer fluid may be added to the wellbore to water wet the wellbore. The addition of a spacer fluid may also be necessary to ensure proper displacement of the drilling mud during the cementing process.

Improper displacement of drilling mud within the wellbore can leave a significant amount of drilling mud at the interface between the cement and the wellbore formation. This can lead to poor cement bonding or multiple problems such as hydrocarbon loss due to migration from one zone to another or to the earth's surface, interactions of the corrosive well fluid to the steel casing, channels of undisplaced mud created "defects" in the cement sheath, and not properly supporting the wellbore. A spacer fluid is often pumped down the wellbore before the cement is pumped into the wellbore to properly displace the drilling mud and water wet the formation and external surface of the casing. Although spacer fluids help in the cementing process, one problem is determining the rheological properties of the spacer fluid to ensure its ability to properly water wet the formation and the casing as well as properly displacing the drilling mud. Additionally, it is difficult to determine the optimal formulation of the spacer fluid, the amount of spacer fluid needed, and/or the amount of surfactant in the spacer that needs to be pumped into the wellbore.

A Water Wetting Capability Tester (WWCT) as set forth in API RP 10B-2, First Edition, may be used to determine the water wettability of a fluid or fluid mixture at atmospheric pressure and at temperatures up to 200° F. The WWCT uses a conductivity probe to determine the water wettability of the tested fluid. It is known in the industry that the water wettability of a fluid may be determined by the conductivity of the fluid. As such, the WWCT includes a conductivity probe placed in the fluid cavity of the apparatus. A spacer fluid may be first tested in the WWCT to determine the conductivity index or water wettability of the spacer fluid. The WWCT can then evaluate the mixture of a known amount of a spacer fluid with a known amount of drilling mud. Typically, enough spacer fluid will be added until the mixture has a water wettability that is substantially equal to the water wettability of the spacer fluid alone.

Although the WWCT may be used to determine the water wettability of the combined mixture, it takes multiple tests. Additionally, the WWCT cannot simulate the downhole conditions above 200° F. and at pressures greater than atmospheric pressure, which are typical conditions that the spacer fluid and drilling mud mixture will be under. The WWCT does include a rotating blade to ensure that the mixture (drilling mud and spacer) are mixed properly during testing. However, while the rotational speed of the blade can be varied to quickly homogenize the added fluids and prevent static areas from forming, the shear rate at which the fluids are being exposed may not be determined due to the geometry of the mixing blades and the configuration of the mixing container. Thus, the WWCT cannot simulate the shear rate under which the fluid mixture will be exposed in the casing or in the casing-formation annulus. The WWCT does include a heater, but the heater is limited to temperatures below to 200° Fahrenheit to avoid boiling the fluid mixture. Tests using the WWCT are conducted at ambient pressure not at pressures present in the wellbore. Presently, no commercial laboratory apparatus can measure continuously the combined effects of temperature and pressure on the spacer to water wet an oil-based coated surface and measure the rheological properties of the spacer, oil-based drilling mud, and/or the combined fluids.

The WWCT also does not provide any information as to the viscosity of the combined mixture. The viscosity of the mixture will vary depending upon the viscosity of the base spacer and the drilling fluids and the proportions of spacer and drilling fluids in the fluid mixtures. The viscosity of the combined mixture at a certain mud to spacer ratio can be determined if desired with a separate apparatus. However, this apparatus can only evaluate a single mixture and cannot capture the change in viscosity as the proportion of spacer and drilling fluid changes. Nor can the existing apparatus conduct this type of evaluation under pressurized conditions.

In light of the foregoing, it would be desirable to provide an apparatus that may continuously determine the Theological properties, such as water wettability and viscosity, under simulated wellbore conditions. Further it would be desirable to provide an apparatus that can be used to simultaneously determine the rheological properties of a second fluid and then determine the rheological properties of a mixture of the two fluids during a real time basis under simulated wellbore conditions. It would also be desirable for an apparatus that may be used to determine the affect specific downhole conditions have on the rheological properties of a fluid.

The present invention is directed to overcoming, or at least reducing the effects of, one or more of the issues set forth above.

SUMMARY OF THE INVENTION

The object of the present disclosure is to provide an apparatus that may determine the rheological properties of a fluid under simulated wellbore conditions, such as pressure, temperature, and shear rate. In one embodiment an apparatus for determining the water wettability of a fluid under simulated downhole conditions is disclosed. The apparatus may include a cell to hold a fluid and a piston that may apply a designated pressure on the fluid within the cell. A piston pump may be used to apply a pressurized fluid to move the piston within the cell. The pressurized fluid may be mineral oil, but could be a number of suitable fluids as would be appreciated by one of ordinary skill in the art having the benefit of this disclosure.

The apparatus includes a motor to rotate a paddle within the cell. The rotation of the paddle may be varied to change the shear rate exerted on the fluid. Additionally, the motor may include a fluid viscosity feedback or rotary torque sensor to determine the viscosity of the fluid under the simulated conditions.

The apparatus may further include a heater that may be able to heat the fluid within the cell to a specified temperature. The specified temperature may be substantially identical to the temperature at a designated location within a wellbore. The apparatus may further include a conductivity probe that is located within the cell. The conductivity probe may provide information concerning the conductivity of the fluid located within the cell. The apparatus may include a computer to electronically store data, chart recorder, or a wettability readout that is electrically connected to the conductivity probe.

The apparatus may be used to test the water wettability of a spacer fluid, a drilling mud, or any other fluid as would be appreciated by one of ordinary skill in the art having the benefit of this disclosure. The apparatus may include a valve in fluid communication with the fluid located within the cell. The valve may be opened to discharge fluid from the cell. The apparatus may include a flow meter to measure the amount of fluid discharged from the cell.

In one embodiment, a system is disclosed for determining the water wettability of a mixture under simulated downhole conditions. The system includes a first cell and a second cell. The first cell is adapted to contain a first fluid and includes a first piston, a first paddle, a first conductivity probe, and a first heater. The first piston may be moved within the first cell to apply a specified pressure on the first fluid contained within the first cell. The first heater may be used to heat the fluid to a simulated wellbore temperature. The first paddle may be used to exert a simulated shear rate on the first fluid. The first conductivity probe may be used to determine the conductivity of the first fluid. The first cell may include a motor to rotate the first paddle. The motor may include a fluid viscosity feedback or a rotary torque sensor that may be used to determine the viscosity of the first fluid under the simulated downhole conditions.

The system includes a second cell adapted to contain a second fluid and includes a second piston, a second paddle, a second conductivity probe, and a second heater. The components of the second cell may determine simulate downhole conditions similar to the first cell. Additionally, the components of the second cell may determine the rheological properties of the second fluid under simulated downhole conditions or the mixture of the two fluids during the conductivity testing.

The system includes first valve in fluid communication with the first fluid and a second valve in fluid communication with the first valve and the second fluid. The first valve and the second valve may be actuated to transfer a portion of the first fluid to the second cell. The system may include a flow meter to measure the portion of first fluid transferred to the second cell. The system includes a wettability readout electrically connected to the conductivity probe in the second cell.

The first piston of the system may apply a pressure of at least 1000 psi to the fluid in the first cell. Likewise, the second piston of the system may apply a pressure of at least 1000 psi to the fluid in the second cell. The first heater may be able to heat the temperature of the fluid in the first cell higher than 200° Fahrenheit. Likewise, the second heater may be able to heat the temperature of the fluid in the second cell higher than 200° Fahrenheit.

In one embodiment, an apparatus is disclosed from determining the water wettability of a fluid under downhole conditions, the apparatus including a cell adapted to contain a fluid and means for applying pressure to a fluid contained within the cell. The apparatus further includes means for mixing the fluid, means for heating the cell, and means for determining the water wettability of the fluid. The means for determining the water wettability of the fluid may be comprised of a conductivity probe. Additionally, the means for determining the water wettability of the fluid may include a readout.

The fluid may be a comprised of a spacer fluid and a drilling mud. The apparatus may further comprise means for determining the viscosity of the fluid. The means for determining the viscosity of the fluid may be a fluid viscosity feedback connected to a motor used to operate the means for mixing the fluid. The viscosity feedback device may be calibrated with a known viscosity fluid such as mineral or silicone oil at the testing temperature and pressure. The means for mixing the fluid may further comprise means for exerting a known shear rate on the fluid. The apparatus may include means for determining the viscosity of the fluid and means for discharging a designated amount of fluid from the cell. The means for discharging a designated amount of fluid from the cell may be an outlet valve in combination with a flow meter.

One embodiment of the present disclosure is a method of determining the wettability of a mixture of a spacer fluid and a drilling mud. The method includes dispensing a spacer fluid into a first cell, applying pressure to the spacer fluid, heating the spacer fluid, and measuring the conductivity of the spacer fluid. The method further includes dispensing a known amount of drilling mud into a second cell, applying pressure to the drilling mud, heating the drilling mud, and measuring the conductivity of the drilling mud. The method further includes transferring a portion of the spacer fluid into the second cell and measuring this amount. The method further includes measuring the conductivity of the drilling mud and spacer fluid combination.

The method may also include adding spacer fluid into the second cell until the conductivity of the combination is substantially equal to the conductivity of the spacer fluid alone. The method may also include applying a known shear force to the fluid in the first cell and applying a known shear force to the fluid in the second cell. The method may further comprise measuring the viscosity of the spacer fluid, the drilling mud, and drilling mud and spacer fluid combination. The viscosity of a fluid may be determined by a fluid viscosity feedback connected to a motor. The method may further include using a sample fluid having a known viscosity to calibrate the fluid viscosity feedback.

Figure 1:
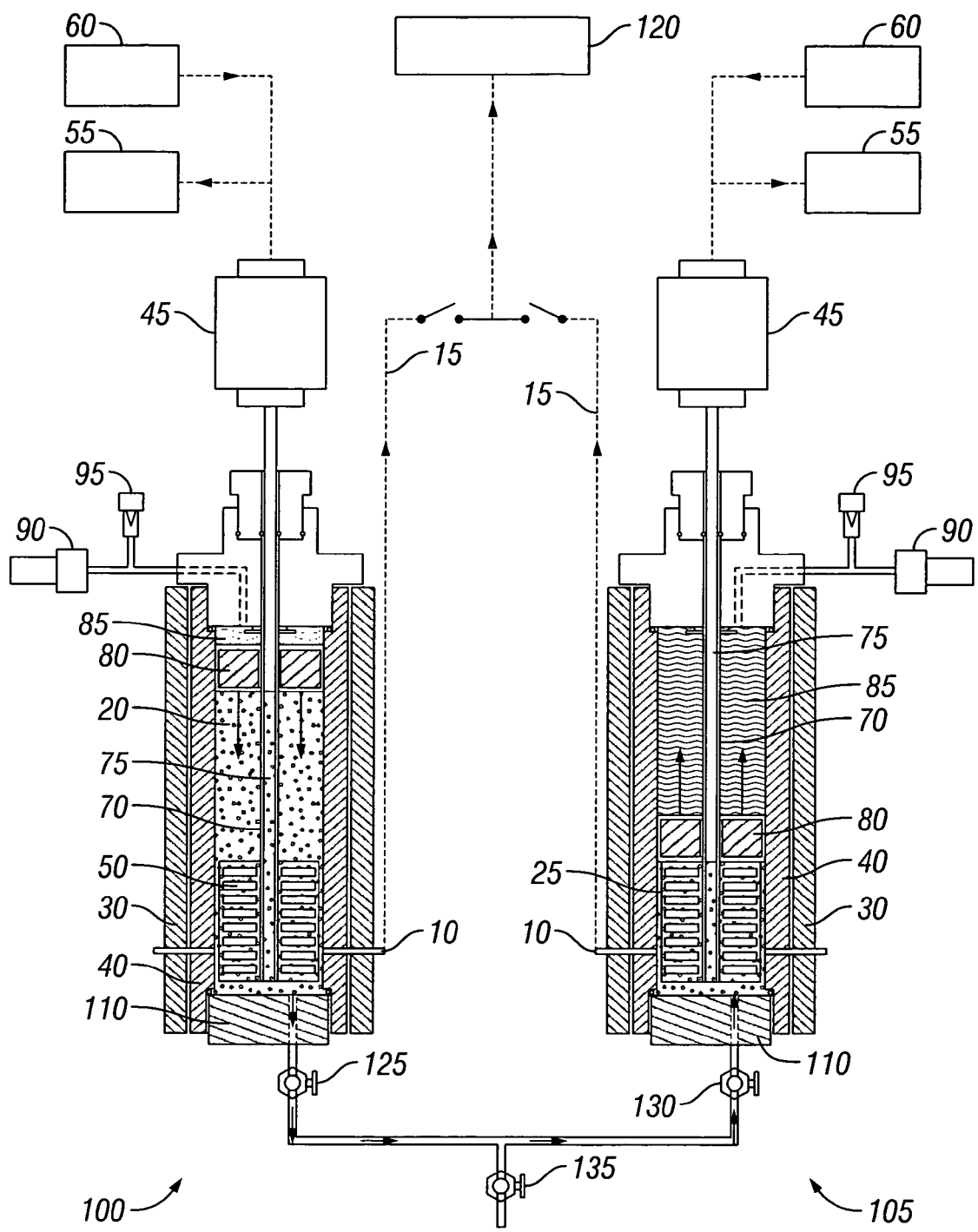
FIG. 1 is a system having a first cell 100 and a second cell 105 used to determine the water wettability of a spacer fluid 20, a drilling mud 25, and a combination of the spacer fluid 20 and drilling mud 25.

While the invention is susceptible to various modifications and alternative forms, specific embodiments have been shown by way of example in the drawings and will be described in detail herein. However, it should be understood that the invention is not intended to be limited to the particular forms disclosed. Rather, the intention is to cover all modifications, equivalents and alternatives falling within the spirit and scope of the invention as defined by the appended claims.

DESCRIPTION OF ILLUSTRATIVE EMBODIMENTS

Illustrative embodiments of the invention are described below as they might be employed in a high temperature fluid test instrument. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments of the invention will become apparent from consideration of the following description and drawings.

FIG. 1 shows an apparatus that may be used to measure the water wettability of a spacer fluid, a drilling mud, and a combination of the spacer fluid with the drilling mud. The apparatus includes a first cell 100 and a second cell 105. The first cell 100 may be comprised of a cell wall 40 and bottom cap 110 that may be used to contain a spacer fluid 20. A conductivity probe 10 is included within the first cell 100 to determine the water wettability of the spacer fluid 20 under downhole conditions. The conductivity probe 10 is electrically connected 15 with a water wettability readout 120.

As discussed above, prior devices have been used to determine the water wettability of a fluid or a fluid mixture using a conductivity probe. However, these prior devices have limitations and were not able to test the fluid or fluid mixture under simulated downhole conditions. For example, the prior device could only measure the conductivity of the fluid at ambient pressure at a specified temperature. Additionally, the prior device did not provide any information concerning the viscosity of the fluid(s) being tested.

The testing apparatus of FIG. 1 includes a piston 80 that may exert a force on the spacer fluid 20 contained within the first cell 100. A pump 90 is used to pump mineral oil 85 to move the piston 80 within the first cell 100 and apply pressure on the spacer fluid 20. The hydraulic line carrying the mineral oil may include a proportional pressure relieve valve 95 as shown in FIG. 1. Mineral oil is a good hydraulic fluid to use with the piston because in the event of a leak the mineral oil will not mix with the spacer fluid. A various number of different fluids could be used in place of the mineral oil as would be appreciated by one of ordinary skill in the art having the benefit of this disclosure. The piston 80 may exert a wide range of pressure on the spacer fluid 20 and may be able to approximately replicate the pressure that will be exerted on the spacer fluid at a designated downhole location.

The first cell 100 also includes a heater 30 to raise the spacer fluid 20 to a designated temperature. The heater 30 may provide for a wide range of temperatures within the first cell 100 to approximately replicate downhole temperatures at a designated downhole location. For example, the heater 30 may be able to raise the temperature the spacer fluid 20 to at least 600° Fahrenheit.

The first cell 100 includes a paddle 50 that is connected to an electric motor 45 by a standpipe 70 having a shaft 75. The paddle 50 may be used to mix the spacer fluid 20 and exert a shear force on the spacer fluid 20. The paddle 50 may be able to approximate the shear force that would be subjected on the spacer fluid 20 at a designated downhole location. The first cell 100 provides that the water wettability of the spacer fluid 20 may be determined under simulated downhole conditions using the heater 30, the paddle 50, and the piston 80.

The first cell 100 may also provide for the viscosity of the spacer fluid 20 under simulated downhole conditions. The electric motor 45 is operated by a controller 60 may include a fluid viscosity feedback 55. The fluid viscosity feedback 55 determines the viscosity of the fluid within the first cell 100 by the amount of torque place on the electric motor 45 by the paddle 50. The fluid viscosity feedback 55 may be calibrated prior to testing the spacer fluid 20 by using a fluid having a known viscosity in the first cell 100.

The bottom cap 110 of the first cell 100 includes an outlet line connected to an outlet valve 125 that is in fluid communication with the spacer fluid 20. The outlet line may include a flow meter that determines that amount of spacer fluid 20 that has been discharged form the first cell 100.

As shown in FIG. 1, the first cell 100 may be used in conjunction with a second cell 105 of identical construction. The outlet line of the first cell 100 may be in fluid communication with an inlet line through the bottom cap 110 of the second cell 105. An inlet valve 130 may be used to control the entry of spacer fluid 20 into the second cell 105. A flow meter may be connected to the inlet line to measure the amount of fluid entering or leaving the second cell 105. Although the system shown in FIG. 1 shows two valves 125, 130 for the transfer of fluid from the first cell 100 to the second cell 105, a single valve and flow meter could be used as would be appreciated by one of ordinary skill in the art having the benefit of this disclosure.

The second cell 105 may be used to determine the water wettability of a drilling mud 25 under simulated downhole conditions. The second cell 105 also includes an electric motor 45 having fluid viscosity feedback, thus allowing the determination of the viscosity of the drilling mud 25 at simulated downhole conditions.

The use of two cells 100, 105 that are fluidly connected provides for the real time testing of a spacer fluid and drilling mud mixture at simulated downhole conditions. Generally, spacer fluid 20 will be discharged from the first cell 100 into the second cell 105 until the water wettability of the mixture substantially equals the water wettability of the spacer fluid 20 alone. The viscosity of the mixture can also be determined under simulated downhole conditions using the fluid viscosity feedback 50 of the second cell. The use of flow meters provides for the amount of spacer fluid 20 that needs to be combined with drilling mud 25 to achieve the requisite water wettability. The system may include a third valve 135 that allows for the fluid from each cell to be drained, if so desired.

Although various embodiments have been shown and described, the invention is not so limited and will be understood to include all such modifications and variations as would be apparent to one skilled in the art.

What is claimed is:

1. An apparatus for determining the water wettability of a fluid under downhole conditions, the apparatus comprising:
    a cell adapted to contain a fluid;
    a piston, the piston adapted to apply pressure to a fluid contained within the cell;
    a paddle, the paddle positioned within the cell;
    a conductivity probe, the conductivity probe located within the cell;
    a heater, the heater may heat the fluid in the cell;
    a wettability readout, the wettability readout electrically connected to the conductivity probe; and
    a pump to pump a fluid to move the piston and apply pressure to the fluid within the cell.

2. The apparatus of claim 1, further comprising a flow meter which measures the portion of fluid transferred from the cell.

3. The apparatus of claim 1 further comprising a motor connected to the paddle, wherein the motor rotates the paddle within the cell.

4. The apparatus of claim 3 wherein the motor includes a fluid viscosity feedback or a rotary torque sensor.

5. The apparatus of claim 1 wherein the rotation of the paddle subjects the fluid in the cell to a shear rate substantially identical to the shear rate exerted on the fluid in the cell under specified downhole conditions.

6. The apparatus of claim 1 wherein the fluid in the cell is a spacer fluid.

7. The apparatus of claim 1 wherein the fluid in the cell is an oil based drilling mud.

8. The apparatus of claim 1 further comprising a valve in fluid communication with the fluid contained in the cell, the valve being configured to transfer at least a portion of the fluid in the cell away from the cell.

9. The apparatus of claim 8, wherein the pump fluid is mineral oil.

10. A system for determining the water wettability of a mixture under downhole conditions, the system comprising:
    a first cell adapted to contain a fluid, the first cell including a first piston adapted to apply pressure to a first fluid contained within the first cell, a first paddle, a first conductivity probe, and a first heater;
    a second cell adapted to contain a fluid, the second cell including a second piston adapted to apply pressure to a second fluid contained within the second cell, a second paddle, a second conductivity probe, and a second heater;
    a first valve in fluid communication with the first fluid of the first cell and in fluid communication with the second fluid of the second cell, wherein a portion of the first fluid may be transferred from the first cell into the second cell;
    a flow meter, the flow meter measures the portion of the first fluid transferred into the second cell; and
    a wettability readout, the wettability readout electrically connected to the first conductivity probe and electrically connected to the second conductivity probe.

11. The system of claim 10 further comprising a second valve in fluid communication with the first valve and in fluid communication the second fluid of the second cell.

12. The system of claim 10 wherein the first fluid is a spacer fluid and the second fluid is a drilling mud.

13. The system of claim 12 further comprising a first motor connected to the first paddle and a second motor connected to the second paddle, wherein the first motor rotates the first paddle and the second motor rotates the second paddle.

14. The system of claim 13 wherein the first motor includes a fluid viscosity feedback or a rotary torque sensor and the second motor includes a fluid viscosity feedback or a rotary torque sensor.

15. The system of claim 10 wherein the first piston can apply a pressure of at least 1000 psi to the fluid in the first cell and the second piston can apply a pressure of at least 1000 psi to the fluid in the second cell.

16. The system of claim 10 wherein the first heater can heat the fluid in the first cell to a temperature over 2000 Fahrenheit and the second heater can heat the fluid in the second cell to a temperature over 2000 Fahrenheit.

17. An apparatus for determining the water wettability of a fluid under downhole conditions, the apparatus comprising:
    a cell adapted to contain a fluid;
    means for applying pressure to a fluid contained within the cell;
    means for mixing the fluid;
    means for heating the fluid in the cell; and
    means for determining the water wettability of the fluid, wherein the means for mixing the fluid may further comprise means for exerting a known shear rate on the fluid.

18. The apparatus of claim 17, further comprising a flow meter which measures the portion of fluid transferred from the cell.

19. The apparatus of claim 17 wherein the fluid comprises a mixture of a spacer fluid and a drilling mud.

20. The apparatus of claim 17 further comprising means for determining the viscosity of the fluid.

21. The apparatus of claim 17 wherein the means for determining the water wettability of the fluid comprises a conductivity probe in electrical communication with a readout.

22. The apparatus of claim 17 further comprising a valve in fluid communication with the fluid contained in the cell, the valve being configured to transfer at least a portion of the fluid away from the cell.

23. A method of determining the wettability of a mixture of a spacer fluid and a drilling mud, the method comprising:
    dispensing a spacer fluid into a first cell;
    applying pressure to the spacer fluid within the first cell;
    heating the spacer fluid within the first cell;
    measuring the conductivity of the spacer fluid;
    dispensing a known amount of drilling mud into a second cell;
    applying pressure to the drilling mud within the second cell;
    heating the drilling mud within the second cell;
    measuring the conductivity of the drilling mud within the second cell;
    transferring a portion of the spacer fluid to the second cell with the drilling mud;
    measuring the amount of spacer fluid transferred into the second cell; and
    measuring the conductivity of the drilling mud and spacer fluid combination.

24. The method of claim 23 further comprising adding spacer fluid into the second cell until the conductivity of the drilling mud and spacer fluid combination is substantially equal to the conductivity of the spacer fluid in the first cell.

25. The method of claim 23 further comprising applying a known shear force to the fluid in the first cell and a known shear force to the fluid in the second cell.

26. The method of claim 25 further comprising measuring the viscosity of the spacer fluid in the first cell.

27. The method of claim 26 further comprising measuring the viscosity of the drilling mud in the second cell.

28. The method of claim 27 further comprising measuring the viscosity of the drilling mud and spacer fluid combination in the second cell.

29. The method of claim 26 wherein a first fluid viscosity feedback connected to a first electric motor is used to measure the viscosity of the spacer fluid.

30. The method of claim 29 wherein a second fluid viscosity feedback connected to a second electric motor is used to measure the viscosity of the drilling mud.

31. The method of claim 30 further comprising measuring the viscosity of a sample fluid having a known viscosity in the second cell to calibrate the second fluid viscosity feedback.

32. The method of claim 29 further comprising measuring the viscosity of a sample fluid having a known viscosity in the first cell to calibrate the first fluid viscosity feedback.

33. The method of claim 23 wherein the pressure applied to the spacer fluid in the first cell and the pressure applied to the drilling mud in the second cell are both substantially equal to a determined downhole pressure.

34. The method of claim 23 wherein the first cell and the second cell are heated to a determined downhole temperature.

35. The method of claim 23 wherein the pressure applied to the spacer fluid in the first cell and the pressure applied to the drilling mud in the second cell are both greater than 1000 psi.

36. The method of claim 23 where the first cell and the second cell are both heated above 2000 Fahrenheit.

37. A system for determining the water wettability of a mixture under downhole conditions, the system comprising:
   a first cell adapted to contain a fluid, the first cell including a first piston adapted to apply pressure to a first fluid contained within the first cell;
   a second cell adapted to contain a fluid, the second cell including a second piston adapted to apply pressure to a second fluid contained within the second cell, wherein a portion of the first fluid may be transferred from the first cell into the second cell; and
   a wettability readout apparatus connected to the system.

38. A system as defined in claim 37, the system further comprising a first conductivity probe connected to the first cell and a second conductivity probe connected to the second cell, the wettability readout apparatus being connected to the first and second conductivity probes.

39. A system as defined in claim 37, the system further comprising a flow meter to measure the portion of the first fluid transferred into the second cell.

40. A system as defined in claim 37, the system further comprising a fluid viscosity feedback or a rotary torque sensor.

* * * * *

UNITED STATES PATENT AND TRADEMARK OFFICE
CERTIFICATE OF CORRECTION

PATENT NO. : 7,743,674 B2  Page 1 of 1
APPLICATION NO. : 11/651089
DATED : June 29, 2010
INVENTOR(S) : Boncan et al.

It is certified that error appears in the above-identified patent and that said Letters Patent is hereby corrected as shown below:

Column 7, Line 67:  after "communication" insert --with--

Column 8, Line 16:  delete "2000" and replace with --200°--

Column 8, Line 18:  delete "2000" and replace with --200°--

Column 10, Line 5:  delete "2000" and replace with --200°--

Signed and Sealed this

Twenty-first Day of September, 2010

David J. Kappos
*Director of the United States Patent and Trademark Office*